United States Patent [19]

Liu et al.

[11] 4,109,014

[45] Aug. 22, 1978

[54] PHARMACEUTICAL, COMPOSITIONS CONTAINING SUBSTITUTED 4'-HYDROXYPHENYL GUANIDINES AND METHODS OF USING SAME

[75] Inventors: Robert Chung-Huan Liu; John Lawrence Hughes, both of Kankakee, Ill.

[73] Assignee: Armour Pharmaceutical Company, Phoenix, Ariz.

[21] Appl. No.: 762,358

[22] Filed: Jan. 25, 1977

Related U.S. Application Data

[60] Division of Ser. No. 518,925, Oct. 29, 1974, Pat. No. 4,014,934, which is a continuation-in-part of Ser. No. 460,815, Apr. 15, 1974, Pat. No. 3,908,013, which is a division of Ser. No. 73,244, Sep. 17, 1970, abandoned.

[51] Int. Cl.² ............................................. A61K 31/155
[52] U.S. Cl. ................................................... 424/326
[58] Field of Search ............................... 424/326, 316

[56] References Cited

PUBLICATIONS

Chem. Abst., vol. 29, col. 1504(8), (1935).

Chem. Abst., vol. 47, col. 3923(b), (1953).

*Primary Examiner*—Albert T. Meyers
*Assistant Examiner*—Daren M. Stephens
*Attorney, Agent, or Firm*—Richard R. Mybeck; Frank T. Barber

[57] ABSTRACT

Novel aromatic guanidine compounds having the formula:

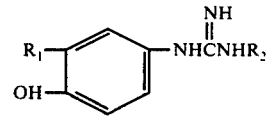

wherein: $R_1$ is hydroxyl, methyl or hydroxymethyl and $R_2$ is hydrogen or methyl, are found to have biological activity. The guanidine compounds and their salts are shown to be active as vasoconstrictor agents and create useful pharmaceutical preparations when deployed with a pharmaceutically acceptable carrier for administration to a host, e.g., man, requiring vasoconstrictive therapy.

6 Claims, No Drawings

PHARMACEUTICAL, COMPOSITIONS CONTAINING SUBSTITUTED 4'-HYDROXYPHENYL GUANIDINES AND METHODS OF USING SAME

This application is a divisional application from our copending U.S. application Ser. No. 518,925, now U.S. Pat. No. 4,014,934, filed on Oct. 29, 1974 as a continuation in part of our then copending U.S. application Ser. No. 460,815, now U.S. Pat. No. 3,908,013, filed on Apr. 15, 1974 as a divisional application of our then copending U.S. application Ser. No. 73,244, filed Sept. 17, 1970, now abandoned.

DESCRIPTION OF INVENTION

This invention relates to generally novel chemical compounds and methods of using them to realize the benefits of their novel biological properties and more particularly to a class of novel aromatic guanidine compounds and their corresponding non-toxic acid addition salts which possess vasoconstrictor properties and hence are useful as vasoconstrictor agents.

The class of compounds embraced with the present invention and for which this patent is sought are represented by the structural notation:

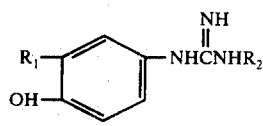

wherein: $R_1$ is hydroxyl, methyl or hydroxymethyl and $R_2$ is hydrogen or methyl. The non-toxic acid addition salts of the guanidine compounds are also biologically active. All of the aforesaid compounds and salts are active vasoconstrictor agents.

Representative of compounds suitable for practice of this invention are: 1-(3',4'-dihydroxyphenyl)-3-methylguanidine; 3',4'-dihydroxyphenylguanidine; 4'-hydroxy-3'-methylphenylguanidine; and 4'-hydroxy-3'-hydroxymethylphenylguanidine. Representative of the salts embodied in this invention are: 1-(3',4'-dihydroxyphenyl)-3-methylguanidine hydrochloride; 3',4'-dihydroxyphenylguanidine hydrochloride; 4'-hydroxy-3'-methylphenylguanidine sulfate; and 4'-hydroxy-3'-hydroxymethylphenylguanidine hydrochloride.

The term "vasoconstrictor agents", as used herein to define the utility of the new compounds of this invention, means those agents which are useful to effect the amelioration of congestive states of the eye and nose, and in treatment of shock and other hypotensive states.

Compounds known previously as vasoconstrictor agents, and the basis of current commercial efforts by the pharmaceutical industry are methoxamine, ephedrine, epinephrine, oxymetazoline, phenylephrine, levartenenol, naphazoline and tuaminoheptane.

While these compounds have been successful in providing the desired vasoconstrictive action, they have also been the cause of severe adverse reactions such as cardiac arrhythmias and excessive elevation of blood pressure. Further, such compounds, when employed in topical formulations are known to cause stinging, burning, and the sensation of intense dryness.

The present invention is predicated upon the discovery of new aromatic guanidine compounds and their corresponding non-toxic acid addition salts shown above, which possess remarkably unexpected properties as vasoconstrictor agents and obtain vasoconstrictor activity without any significant changes in the cardiac rate of the host to whom such agents are administered. Further, as will appear, the compounds of this invention may be administered by oral, parenteral and topical routes with but minimal effects on the cardiac rate of the host animal, including man.

Accordingly, one of the prime objects of the present invention is to provide new chemical compounds which have biological activity and are useful as vasoconstrictor agents.

A further object of the present invention is to provide new aromatic guanidine compounds which, per se, and in the form of the corresponding non-toxic acid addition salts can be employed as vasoconstrictor agents and are free from significant effects on the cardiac rate of the host to whom it is administered.

Still another object of the present invention is to provide new aromatic guanidine compounds and methods of using them which are useful pharmaceuticals in the treatment of hypotensive states, and as nasal and ocular decongestants.

These and still further objects as shall hereinafter appear are fulfilled by the present invention in a remarkably unobvious fashion as will be discerned from the following detailed description and examples of embodiments of this invention.

The aromatic guanidine compounds of the present invention can be prepared by any of several procedures, for example, the addition of hydrogen cyanamide to an aromatic amine (or its mineral acid addition salts); the reaction of a 1-aryl-2-methyl-2-thiopseudourea hydroiodide with ammonia or an alkyl amine and the like.

The guanidines may be converted to their acid addition salts by reacting the guanidine with an appropriate mineral or organic acid such, for example, as hydrochloric acid, sulfuric acid, nitric acid, hydrobromic acid, hydroiodic acid, maleic acid, citric acid, acetic acid, tartaric acid, benzoic acid, propionic acid, carbonic acid, and like acids which are well known to form pharmaceutically acceptable salts so do not need to be belabored here.

One such procedure for preparing the guanidines comprises the mixture of the appropriate aromatic amine mineral acid addition salt (or the aromatic amine with one molar equivalent of the appropriate mineral acid), aqueous 50% cyanamide solution and ethyl alcohol which is then heated at reflux for 3 to 20 hours. For optimum yield the molar ratio of aromatic amine salt, cyanamide, and ethyl alcohol was 1.0:1.5:15 respectively. The products, i.e., the aromatic guanidine mineral acid addition salts, are isolated from the reaction mixtures and purified by recrystallization from an appropriate solvent, i.e., water or aliphatic alcohols. When the acid addition salt could not be purified it was converted to the free base by the addition of an alkali hydroxide and purified by recrystallization from an appropriate solvent.

Another satisfactory method comprises forming a mixture of an appropriate 1-aryl-2-methyl-2-thiopseudourea hydroiodide, an appropriate primary amine and ethyl alcohol. The mixture is heated at reflux for 20 hours. For optimum yield the molar ratio of the thiopseudourea, primary amine and ethyl alcohol was 1:3:15, respectively. The products are isolated from their reaction mixtures and converted to hydrochloride salts for purification and characterization.

Dihydroxy substituted guanidines are prepared by the method comprising the hydrogenolytic debenzylation, in the presence of palladium catalyst, of the corresponding 3',4'-dibenzyloxyphenylguanidine hydrochloride salts. The reaction procedure is accomplished by agitation of the solution of the benzyloxy compounds in ethyl alcohol in the presence of 5% palladium on powdered charcoal under a hydrogen pressure of 50 psi. The products, after removal of the catalyst, are purified by recrystallization from an appropriate aliphatic alcohol.

A guanidine compound, prepared by either of the foregoing procedures, or by other suitable procedures, may be converted to its acid addition salt, e.g., hydrochloride by the addition of the appropriate acid to the guanidine compound.

The guanidine compounds of this invention may be employed as free bases or in the form of their non-toxic pharmaceutically acceptable salts. Thus, for example, organic and inorganic acid addition salts may be employed, such as the salts of hydrochloric, sulfuric, nitric, phosphoric, citric, acetic, lactic, tartaric, sulfamic, succinic, fumaric, maleic, ethanedisulfonic, hydrobromic, benzoic and similar non-toxic acids. The salts may be prepared by reacting the guanidine base with an excess of acid in a suitable solvent, such as ethanol, acetone, water, or mixture thereof. The mixture is heated to effect solution, and the salts crystallize on cooling.

The guanidines and their salts are administered in therapeutically effective amounts to animals, including man, and in appropriate ways. Thus, dosages of about 1 milligram to 5 milligrams per kilogram of host body weight, may be provided to man by systemic administration, e.g., orally or parenterally. The compounds may be administered systemically to animals other than man in dosages of up to about 5 milligrams per kilogram of body weight. The foregoing and other dosage levels herein are based on the content of guanidine base. The compounds have excellant vasoconstriction, a low order of toxicity, and relatively few observed side effects.

In the preferred embodiments of the invention, an aromatic guanidine or a salt thereof is administered in a pharmaceutical composition which includes the guanidine compound and a pharmaceutical carrier. The carrier is a non-toxic pharmaceutical grade substance, which may be either solid or liquid. Suitable solid carriers include lactose, magnesium stearate, starch, sucrose, mannitol, sorbitol, cellulose powder, dicalcium phosphate, talc, stearic acid, gelatin, agar pectin, acacia and the like. Suitable liquid carriers include glycols, polyglycols, dimethylsulfoxide, peanut oil, olive oil, seseame oil, alcohols, water, and the like. If desired, the carrier may include a time delay material such as glycerol monostearate, or glycerol di-stearate, alone or with a wax.

The composition preferably is provided in unit dosage form for accuracy and convenience in administration. Where appropriate, oral administration is effective and preferred, and dosage units suitable for oral administration are provided. Examples of such dosage units employing solid carriers include tablets, filled capsules, packets and the like, and lozenges. The amount of solid carrier per dosage unit may vary widely, preferably from about 25 milligrams to 5 gram.

The guanidines and their salts may be compounded with semi-solid and liquid carriers in solutions, suspensions, emulsions, ointments, suppositories and soft gelatin capsules, for example. Such compositions may be administered pancavally, i.e., via natural and artificial openings in the body, such as the mouth, the anus, the vagina, the nares, and the stoma of colostomy patients, intravenously or intramuscularly, employing the appropriate composition having a suitable concentration of active ingredient according to the desired route of administration.

The foregoing dosage forms are prepared by conventional procedures of mixing, granulating, compressing, suspending and/or dissolving, as is suitable to prepare the desired dosage form.

The vasoconstriction of a host animal, including man, which has a condition requiring such treatment is readily obtained by administering to the afflicted host an aromatic guanidine or a pharmaceutically acceptable acid addition salt thereof in an amount sufficient to alleviate the symptoms of the condition. The usual symptoms requiring treatment are low blood pressure, ocular and nasal congestion, and the like.

The compound preferably is administered at the dosage level described above and preferably in a pharmaceutical carrier. The dosage level and frequency of administration are to a certain extent subjective, attention being given to the degree of vasoconstriction or decongestion, the case history, the reaction of the subject, and the like.

The daily dosage can be administered in one or more parts and the administration can be accomplished pancavally or parenterally or topically. Administration for the provision of systemic vasoconstriction is preferably oral and is most conveniently accomplished by means of a tablet containing one of the active compounds and a pharmaceutical carrier. For local vasoconstriction, that is, eyes, nose, etc., topical administration is preferred.

We have obtained especially good results when administering to the animal organism the following aromatic guanidines to obtain vasoconstriction therein. The guanidines so used are: 1-(3',4'-dihydroxyphenyl)-3-methylguanidine; 3',4'-dihydroxyphenylguanidine; 4'-hydroxy-3'-methylphenylguanidine; 1-(3',4'-dihydroxyphenyl)-3-methylguanidine hydrochloride; 3',4'-dihydroxyphenylguanidine hydrochloride; 4'-hydroxy-3'-hydroxymethylphenylguanidine hydrochloride.

The onset of activity after oral administration in the animal organism is rapid, results being observed within one-half hour, and the activity is sustained. Thus, the activity levels remain high for two or more hours, and activity persists over a 24-hour period. After topical or intravenous administration the onset of action is rapid and persists for one or more hours.

Of the aromatic guanidines which may be employed to produce vasoconstriction or decongestion, those having meta and/or para substitution appear to provide most desirable results.

The following examples are illustrative of the preparation of the novel guanidines of the invention, new pharmaceutical compositions embodying said guanidines and their non-toxic acid addition salts, the treatment of the animal organism in accordance with the invention, and the activities exhibited in such treatment. It is to be understood that the invention is not limited to the examples or to the compounds, compositions, proportions, conditions, and methods set forth therein, which are only illustrative. Throughout the examples, the specific guanidines enumerated have been used to typify the entire class of compounds and compositions of the invention.

EXAMPLE I 1-(3',4'-Dibenzyloxyphenyl)-3-methylguanidine hydrochloride was prepared from a mixture of 60.6 gm (0.1 mole) of 1-(3,4-dibenzyloxyphenyl)-2-methyl-2-thiopseudourea hydroiodide, 20 gm of aqueous 40 percent methylamine solution (equivalent to 0.65 mole of methylamine), and 250 ml of ethyl alcohol. The mixture was heated at reflux for 20 hours. The reaction mixture was then evaporated to dryness and the residue mixed with 250 ml of water and 40 ml of 10N sodium hydroxide solution. This mixture was extracted with 500 ml of benzene. The benzene extract was washed with 200 ml of water and the benzene layer was evaporated to a viscous residue. This residue was next dissolved in 250 ml of acetone and a solution of hydrogen chloride in ether was added to precipitate the hydrochloride salt of 1-(3',4'-dibenzyloxyphenyl)-3-methylguanidine. This salt after collection and recyrstallization from acetone and ether (2:1 ratio) melted at 158°–60° C.

Analysis: Calcd. for $C_{22}H_{24}ClN_3O_2$: C, 66.40; H, 6.08; Cl, 8.91; N, 10.56. Found: C, 66.20; H, 6.12; Cl, 9.02; N, 10.76.

EXAMPLE II 1-(3',4'-Dihydroxyphenyl)-3-methylguanidine hydrochloride is prepared from a mixture of 28 gm (0.07 mole) of the 1-(3',4'-dibenzyloxyphenyl)-3-methylguanidine hydrochloride (prepared in Example I), 1.0 gm of 5 percent palladium on charcoal, and 250 ml of ethyl alcohol. The mixture was shaken under an initial hydrogen pressure of 50 psi and, after 4 hours of agitation, the reaction mixture was filtered and the filtrate evaporated to a thick residue which solidified after standing 2 hours. This solid was purified by recrystallization from a mixture of ethyl alcohol and ether (3:2 ratio). The resulting white crystalline solid melted at 185°–8° C and the infrared spectrum was consistent with the assigned structure.

Analysis: Calcd. for $C_8H_{12}ClN_3O_2$: C, 44.12; H, 5.56; Cl, 16.28; N, 19.30. Found: C, 44.07; H, 5.64; Cl, 16.50; N, 19.42.

EXAMPLE III

3',4'-dibenzyloxyphenylguanidine was prepared from a mixture of 34 gm (0.1 mole) of 3,4-dibenzyloxyaniline hydrochloride, 12.6 gm of a 50 percent aqueous cyanamide solution (equivalent to 0.15 mole of cyanamide) and 100 ml of ethyl alcohol. The mixture was heated at reflux for 20 hours. This reaction mixture was evaporated to a viscous residue. The residue was mixed with 300 ml of water and then the mixture made basic (pH about 10) by the addition of aqueous 10N sodium hydroxide solution. The mixture was cooled at 0° C for 6 hours and the precipitated solid was collected on a filter. This solid was purified by consecutive recrystallization, first from aqueous 60% methyl alcohol and finally from benzene. The white crystalline solid melted at 138°–9° C. The infrared spectrum was consistent with the structure of the 3',4'-dibenzyloxyphenylguanidine.

Analysis: Calcd. for $C_{21}H_{21}N_3O_2$: C, 72.60; H, 6.09; N, 12.10. Found: C, 72,60; H, 6.24; N, 12.22.

EXAMPLE VI

3',4'-Dihydroxyphenylguanidine hydrochloride was prepared from a mixture of 24.4 gm (0.07 mole) of 3',4'-dibenzyloxyphenylguanidine, 6.9 gm of concentrated hydrochloric acid (equivalent to 0.07 mole hydrogen chloride), 250 ml of ethyl alcohol, and 10 gm of 5 percent palladium on charcoal. The mixture was shaken under an initial hydrogen pressure of 50 psi for 4 hours and then the reaction mixture was filtered and the filtrate evaporated to a thick residue. This residue was then dissolved in a 1:1 mixture of isopropyl alochol and cyclohexane. The solution was cooled at 0° C for 24 hours. The precipitated solid, collected on a filter and dried, melted at 156°–8° C. The infrared spectrum was consistent with the assigned structure for 3',4'-dihyroxyphenylguanidine hydrochloride.

Analysis: Calcd. for $C_7H_{10}ClN_3O_2$: C, 41,29; H, 4.95; Cl, 17.41; N, 20.64. Found: C, 41,51; H, 4.99; Cl, 17.21; N, 20.68.

EXAMPLE V

4'-hydroxy-m-tolylguanidine sulfate was prepared from a mixture of 34.4 gm (0.1 mole) of 4-hydroxy-3-methylaniline sulfate, 12.6 gm of a 50 percent aqueous cyanamide solution (equivalent to 0.15 mole of cyanamide) and 100 ml of ethyl alcohol. The mixture was heated at reflux for 20 hours and the reaction mixture was cooled at 0° C for 5 hours and filtered. The collected solid was purified by recrystallization from aqueous 75 percent ethyl alcohol. The white crystalline solid melted at 268°–70° C (dec.). The infrared spectrum was consistent with the assigned structure.

Analysis: Calcd. for $C_{16}H_{24}N_6O_6S$: C, 44.85; H, 5.65; N, 19.62; S, 7.48. Found: C, 44.95; H, 5.57; N, 19.61; S, 7.48.

EXAMPLE VI

4'-Hydroxy-3'-hydroxymethylphenylguanidine hydrochloride was prepared using the reaction procedure of Example III except 4-hydroxy-3-hydroxymethylaniline hydrochloride was used in place of the 3,4-dibenzyloxyaniline hydrochloride. The reaction mixture was evaporated to a viscous residue which was triturated with a 1:1 mixture of isopropyl alcohol and ethyl acetate. The residual solid was purified by recrystallization from a 1:1 mixture of isopropyl alcohol and ether. The purified yellow crystalline solid melted at 157°–9° C (dec.). The infrared spectrum was consistent with the assigned structure.

Analysis: Calcd. for $C_8H_{12}ClN_3O_2$: C, 44.15; H, 5.56; N, 19.31. Found: C, 44,12; H, 5.67; N, 19.10.

EXAMPLE VII

The following are examples of several dosage forms useful for the practice of the present invention using oral administration.

| FORMULATION "A" | |
|---|---|
| Ingredient | Parts |
| Guanidine Compound | 60 – 300 |
| Calcium Carbonate | 300 |
| Citric Acid (Anhydrous) | 290 |
| Magnesium Carbonate | 129 |
| FORMULATION "B" | |
| Ingredient | Parts |
| Guanidine Compound | 60 – 300 |
| Citric Acid (Anhydrous) | 1000 |
| Sodium Bicarbonate | 2000 |
| Monocalcium Phosphate | 200 |
| FORMULATION "C" | |
| Ingredient | Parts |
| Guanidine Compound | 60 – 300 |
| Corn Starch | 25 – 50 |
| Lactose | 25 – 2000 |
| Magnesium Stearate | 1 – 5 |

-continued

| FORMULATION "D" | |
|---|---|
| Ingredient | Parts |
| Guanidine Compound | 60  60  300 |
| Corn Starch | 25 – 50 |
| Lactose | 25 – 200 |
| Talc | 10 – 50 |
| Silica (Powdered) | 0.1 – 2 |

| FORMULATION "E" | |
|---|---|
| Ingredient | Parts |
| Guanidine Compound | 60  α 30 |
| Lactose | γ– 190 |
| Cellulose | 10 – 135 |
| Magnesium Stearate | 0.1 – 5 |

| FORMULATION "F" | |
|---|---|
| Ingredient | Parts |
| Guanidine Compound | 60 – 300 |
| Cellulose | 15 – 200 |
| Corn Starch | 10 – 50 |
| Gelatin | 5 – 35 |
| Stearic Acid | 15 |

| FORMULATION "G" | |
|---|---|
| Ingredient | Parts |
| Guanidine Compound | 60 – 300 |
| Tricalcium Phosphate | 50 – 150 |
| Corn Starch | 10 – 50 |
| Acacia | 5 – 25 |
| Magnesium Stearate | 1 – 5 |

In each instance, the ingredients in the proportions indicated are milled to a uniform powder, sized, mixed with binder and compressed into tablets.

EXAMPLE VII

Suppositories melting at about 60° F and each having the following composition are produced by compounding the ingredients in the relative proportions indicated and heating the ingredients to about 60° F to effect a solution. The solution is then poured into cooled molds and allowed to cool and solidify.

| Ingredient | Amount |
|---|---|
| Guanidine Compound | 0.1 to 1.0 mg |
| Base of lactose, polyethylene glycol, polyethylene glycol 400, polyethylene glycol 4000, polysorbate 80 and glycerine | 1 gram |

EXAMPLE IX

A glosset for sublingual administration was prepared using 60 to 300 mg of guanidine compound disposed in a rapidly disintegrating base formed of starch, lactose, sodium saccharin and talcum.

EXAMPLE X

The ingredients of the following compositions were compounded to provide a solution suitable for intravenous administration. In each instance, the ingredients were mixed and warmed to about 50°–60° C with stirring to effect solution. The solution was then sterile filtered, cooled to room temperature, and packaged in sterile vials.

| FORMULATION "H" | |
|---|---|
| Ingredient | Amount |
| Guanidine Compound | 10 – 500 mg |
| Sodium Chloride | 890 mg |
| Water | 99 g |

| FORMULATION "I" | |
|---|---|
| Ingredient | Amount |
| Guanidine Compound | 10 – 500 mg |
| Glucose | 5 g |
| Water | 95 g |

EXAMPLE XI

The ingredients of the following compositions were compounded to provide a solution suitable for intramuscular and subcutaneous formulations administration. In each instance, the ingredients were mixed and warmed to about 50°–60° C with stirring to effect solution. The solution was then sterile filtered, cooled to room temperature and packaged in sterile vials.

| FORMULATION "J" | |
|---|---|
| Ingredient | Amount |
| Guanidine Compound | 10 – 500 mg |
| 16% Aqueous Gelatin Containing 0.5% Phenol | 100 g |

| FORMULATION "K" | |
|---|---|
| Ingredient | Amount |
| Guanidine Compound | 10 – 500 mg |
| Sodium Chloride | 890 g |
| Water | 99 g |

| FORMULATION "L" | |
|---|---|
| Ingredient | Amount |
| Guanidine Compound | 10 – 500 mg |
| Glucose | 5 g |
| Water | 95 g |

| FORMULATION "M" | |
|---|---|
| Ingredient | Amount |
| Guanidine Compound | 10 – 500 mg |
| 10–90% Aqueous Polyethylene Glycol 400 | 100 g |

EXAMPLE XII

The guanidine compound is dispersed in a cream vehicle consisting of a water-miscible base of stearic acid, proplylene glycol, sorbitol monostearate and mono-oleate, polyoxyethylene sorbitan monostearate with citric acid and methyl and propyl parabens as preservatives. Concentration of the guanidine compound is 0.1 to 50 mg per gram of vehicle.

Alternately, the guanidine compound may be dispersed in corn oil, sesame oil, cotton seed oil, peanut oil, or polyethylene glycols with the addition of appropriate preservatives.

EXAMPLE XIII

The vasoconstrictor properties of several representative compounds of this invention were determined pharmacologically using accepted methodology. The heart rate changes in anesthetized dogs who received an intravenous dosage of a guanidine compound as indicated. Throughout the procedure, host blood pressure was monitored by means of an indwelling arterial catheter connected to a pressure transducer, host heart rate was determined from the limb electrocardiogram, and carotid arterial blood flow was continuously monitored with a flow probe around the artery which probe was connected to an electromagnetic flow meter. It will be noted that three standard vasoconstrictors, all current commercial products, were also assayed in this manner and provide a reference base. The test compounds are coded in Table I and the data is reported in subsequent tables below.

TABLE I

| Test Compound Code | Chemical Name |
|---|---|
| A | 1-(3',4'-Dihydroxyphenyl)-3-methyl guanidine hydrochloride |
| B | 3',4'-Dihydroxyphenyl guanidine hydrochloride |
| C | 4'-Hydroxy-m-tolyl guanidine sulfate |
| D | 4'-Hydroxy-3'-hydroxymethyl phenyl guanidine hydrochloride |

TABLE II

Heart Rate Changes in Anesthetized Dogs

| Test Compound | Dose (mg/Kg.i.v.) | | |
|---|---|---|---|
| | 0.01 | 0.1 | 1.0 |
| A | 0 | + | + |
| B | − | − | + |
| C | 0 | − | − |
| D | 0 | − | − |
| Naphazoline | − | − | + |
| Phenylephrine | − | + | + |
| Phenylpropanolamine | 0 | + − | − |

Rating Scale:
− Decrease in heart rate
0 No change in heart rate
+ Increase in heart rate

EXAMPLE XIV

Additional data was obtained for each respresentative compound by measuring the rise in mean arterial blood pressure after intravenous administration to an anesthetized dog.

The scale employed to evaluate the results is shown in Table III, and the test data is recorded in Table IV, using the code for test compounds set forth in Table I of Example XIII.

TABLE III

| Activity Rating | Pressure Rise in mm Hg |
|---|---|
| 0 | 0 – 3 |
| 1 | 4 – 10 |
| 2 | 11 – 25 |
| 3 | 26 – 50 |
| 4 | 51 – 75 |
| 5 | >75 |

TABLE IV

Activity Rating for Test Compounds

| Test Compound | Dose (mg/Kg.i.v.) | | |
|---|---|---|---|
| | 0.0. | 0.1 | 1.0 |
| A | 0 | 3 | 5 |
| B | 2 | 3 | 5 |
| C | 1 | 3 | 5 |
| D | 3 | 4 | 5 |
| Naphazoline | 3 | 4 | 4 |
| Phenylephrine | 3 | 5 | 5 |
| Phenylpropanolamine | 0 | 3 | 5 |

EXAMPLE XV

An aqueous solution was prepared containing 3',4'-dihydroxyphenylguanidine hydrochloride and suitable for use with the nose and eyes to effect decongestion of the mucous membranes of these organs. The solution was stable, physiologically isotonic and had a pH in the range of 6 to 7.

The formulation is shown below. The sodium phosphate salts comprise a buffer system to maintain the pH at about 6.5 and sodium bisulfite is used as an antioxidant. Sodium chloride provides the desired isotonicity and Thimerosal as a preservative which protects the solution from bacterial and mold contamination.

| FORMULATION "N" | |
|---|---|
| Ingredient | Wt. % |
| 3',4'-Dihydroxyphenyl-guanidine hydrochloride | 2.00 |
| Monbasic Sodium Phosphate | 0.10 |
| Dibasic Sodium Phosphate | 0.12 |
| Sodium Bisulfate | 0.20 |
| Sodium Chloride | 0.15 |
| Merthiolate Sodium (Thimerosal) | 0.01 |
| Water | 97.42 |

From the foregoing, it becomes apparent that the invention herein described and illustrated fulfills all of our objectives, express and implied, in a remarkably unexpected fashion and that we have developed new and useful compounds, pharmaceutical compositions and therapeutic methods for providing vasoconstriction in hosts requiring such therapy.

What is claimed is:

1. A pharmaceutical composition consisting of a pharmaceutical grade carrier and a therapeutically effective vasoconstrictive amount of a guanidine compound of a non-toxic acid addition salt thereof, said compound having the formula:

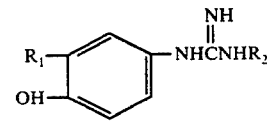

wherein: $R_1$ is hydroxyl, methyl or hydroxymethyl; and $R_2$ is hydrogen or methyl.

2. A composition according to claim 1 wherein said addition salt is 3',4'-dihydroxyphenylguanidine hydrochloride.

3. A composition according to claim 1 wherein said addition salt is 4'-hydroxy-m-tolylguanidine sulfate.

4. A composition according to claim 1 wherein said addition salt is 4'-hydroxy-3'-hydroxymethylphenylguanidine hydrochloride.

5. A pharmaceutical composition according to claim 1 in a dosage unit form selected from the group consisting of tablets, filled capsules, packets, lozenges, glossets, sterile solutions, suspensions, emulsions, ointments, suppositories and soft gelatin capsules.

6. The method of treating a host requiring vasoconstriction comprising administering to said host from about 1 mg to about 5 mg per kilogram of host body weight of a compound according to claim 1 or a non-toxic acid addition salt thereof to provide vasoconstriction in said host.

* * * * *